United States Patent [19]

Griffith et al.

[11] Patent Number: 5,395,612
[45] Date of Patent: Mar. 7, 1995

[54] METHOD FOR TREATING SYSTEMIC HYPOTENSION CAUSED BY SEPSIS OR CYTOKINE USING ARGINASE IN COMBINATION WITH AN $\alpha_1$ ADRENERGIC AGONIST

[75] Inventors: Owen W. Griffith, Milwaukee, Wis.; Steven S. Gross; Roberto Levi, both of New York, N.Y.

[73] Assignee: Cornell Research Foundation, Inc., Ithaca, N.Y.

[21] Appl. No.: 814,808

[22] Filed: Dec. 31, 1991

Related U.S. Application Data

[63] Continuation-in-part of Ser. No. 499,610, Mar. 27, 1990, Pat. No. 5,196,195.

[51] Int. Cl.$^6$ ............................................. A61K 37/54
[52] U.S. Cl. ............................................... 424/94.6
[58] Field of Search .................. 435/1, 240.1, 240.2, 435/240.3, 240.31; 514/564, 2; 424/94.6

[56] References Cited

U.S. PATENT DOCUMENTS

| | | | |
|---|---|---|---|
| 2,663,668 | 12/1953 | Vrat | 424/94.6 |
| 2,834,713 | 5/1958 | Robbins | 435/227 |
| 4,282,217 | 8/1981 | Baglioni et al. | 514/179 |
| 4,734,438 | 3/1988 | Macri | 514/653 |
| 5,028,627 | 7/1991 | Kilbourn et al. | 514/565 |
| 5,059,712 | 10/1991 | Griffith | 562/560 |
| 5,196,195 | 3/1993 | Griffith | 424/94.6 |
| 5,216,025 | 6/1993 | Gross et al. | 514/565 |
| 5,286,739 | 2/1994 | Kilbourn et al. | 514/400 |

FOREIGN PATENT DOCUMENTS 2126181 12/1971 Germany ................ 424/94.6
PCT/US/90-
/05199 9/1990 WIPO.

OTHER PUBLICATIONS

Ramanathan S et al, Acta Anaesthesiol Scand. 32:559–65 (1988).
Thermermann C et al, Eur. J. Pharmacol 182:591–5 (1990).
Aisaka, K., Biochemical and Biophysical Research Communications, 163, No. 2, 710–717 (Sep. 1989).
Hibbs, J. B., et al, The Journal of Immunology, 138, No. 2, 550–565 (1987).
Jackson, J. A., et al, J. Pharmacol. Expt. Ther. 209, 271–274 (1979).
Ko, R. Y. C., et al, J. Biomed. Res. 10, 249–258 (1976).
Olanoff, L. S., et al, J. Biomed. Res. 8, 125–136 (1977).
Savoka, K. V., et al, Biochem. Biophys. Acta 578, 47–53 (1979).
Blethen, S. L., et al, J. Biol. Chem., vol. 243, No. 8, 1671–1677 (1968).
Mitchell, J. A., et al, European Journal of Pharmacology, 182, 573–576 (1990).
Olken, N. M., et al, Biochem. Biophys. Res. Comm., vol. 177, No. 2, 828–833 (Jun. 14, 1991).
Stuehr, D. J., et al, Proc. Natl. Acad. Sci. USA, vol. 88, 7773–7777 (Sep. 1991).
Taylor, H., et al (ed.), Methods in Enzymology, vol. XVIIA, pp. 310–317, 335–340, Academic Press, 1970.
Yui, Y., et al, J. Biol. Chem., vol. 266, No. 19, 12544–12547, 1991.

(List continued on next page.)

Primary Examiner—Douglas W. Robinson
Assistant Examiner—Sandra Saucier

[57] ABSTRACT

Reducing plasma levels of endogenous arginine by parenteral administration of arginine depleting agent limits nitric oxide formation and results in blood pressure increase. Preferably arginase is administered intravenously to raise blood pressure. The arginine depleting agent can be administered in conjunction with arginine antagonists to potentiate the effect of these. The arginine depleting agent can be used concurrently with $\alpha_1$ adrenergic agonists in treating systemic hypotension caused by induced production of nitric oxide, to restore vascular contractile sensitivity to the effect of the $\alpha_1$ adrenergic agonists. Duration of action and avoidance of antigenicity may be obtained by use in conjunction with a carrier or modifier.

5 Claims, 2 Drawing Sheets

OTHER PUBLICATIONS

Stuehr, D. J. et al, Synthesis of Nitrogen Oxides from L-Arginine by Macrophage Cytosol: Requirement for Inducible and Constitutive Components, *Biochem, Biophys. Res. Commun.*, (1989) vol. 161, 420–426.

Stuehr, D. J. et al., Activated Murine Macrophages Secrete a Metabolite of Arginine with the Bioactivity of Endothelium–Derived Relaxing Factor and the Chemical Reactivity of Nitric Oxide, *J. Exp. Med.*, (1989) vol. 169, 1011–1020.

Rees, D. D. et al., Role of Endothelium–Derived Nitric Oxide in the Regulation of Blood Pressure, *Proc. Natl. Acad. Sci. U.S.A.*, (1989) vol. 86, 3375–3378.

Aisaka, K. et al., $N^G$-Methylarginine, An Inhibitor of Endothelium–Derived Nitric Oxide Synthesis, is a Potent Pressor Agent in the Guinea Pig: Does Nitric Oxide Regulate Blood Pressure in vivo, *Biochem. Biophys. Res. Commun.* (1989), 160:881–886.

Natanson, C. et al., Endotoxin and Tumor Necrosis Factor Challenges in Dogs Simulate the Cardiovascular Profile of Human Septic Shock, *Journal of Exp. Med.* (1989) 169:823–832.

Schmidt, H. et al., Arginine is a Physiological Precursor of Endothelium–Derived Nitric Oxide, *Eur. J. of Pharmacology* (1988) 154:213–216.

Palmer, R. M. J. et al., L-Arginine is the Physiological Precursor for the Formation of Nitric Oxide in Endothelium-Dependent Relaxation, *Biochem. Biophys. Res. Commun.* (1988) 153:1251–1256.

Sakuma, I. et al., Identification of Arginine as a Precursor of Endothelium–Derived Relaxing Factor, *Proc. Natl. Acad. Sci U.S.A.* (1988) 85:8664–8667.

Palmer, R. M. J. et al., Vascular Endothelial Cells Synthesize Nitric Oxide from Arginine, *Nature*, (1988) vol. 333, 664–666.

Hibbs, J. B. et al., Nitric Oxide: A Cytotoxic Activated Macrophage Effector Molecule, *Biochem. Biophys. Res. Commun.* (1988) 157:87–94.

Marletta, M. A. et al., Macrophage Oxidation of L-Arginine to Nitrite and Nitrate: Nitric Oxide Is an Intermediate, *Biochemistry* (1988) 27:8706–8711.

Palmer, R. M. J. et al., Nitric Oxide Release Accounts for the Biological Activity of Endothelium–Derived Relaxing Factor, *Nature* (1987) 327:524–526.

Stuehr, D. J. et al., Induction of Nitrite/Nitrate Synthesis in Murine Macrophages by BCG Infection, Lymphokines, or Interferon-$\gamma$, *J. of Immunology* (1987) 139:518–525.

Iyengar, R. et al., Macrophage Synthesis of Nitrite, Nitrate and N-Nitrosamines: Precursors and Role of the Respiratory Burst, *Proc. Natl Acad. Sci. U.S.A.* (1987) vol. 84, 6369–6373.

Turan, et al., *Acta Chimica Academiae Scientiarum Hungaricae* (1975) 85:327–332.

Kilbourn et al., $N^G$-Methyl-L-Arginine Inhibits Tumor Necrosis Factor–Induced Hypotension: Implications for the Involvement of Nitric Oxide *Proc. Natl. Sci. U.S.A.* (1990) 87:3629–3632.

Gray, G. A., et al, *Br. J. Pharmacol.*, 103, 1218–1224 (1991).

Julou-Schaeffer, G., et al, *Am. J. Physiol.* 259, H1038–H1043, (1990).

Billar, T. R., *Journal of Leukocyte Biology* 48:565–569 (1990).

Moncada, S., et al, *Pharmacological Reviews* 43(2):109–142 (1991).

Griffith, O. W., et al, The Role of Plasma Arginine in Nitric Oxide Synthesis: Studies with Arginase–Treated Rats, from the Book of Abstracts, Second International Meeting "Biology of Nitric Oxide", handed out Sep. 29, 1991.

METHOD FOR TREATING SYSTEMIC HYPOTENSION CAUSED BY SEPSIS OR CYTOKINE USING ARGINASE IN COMBINATION WITH AN $\alpha_1$ ADRENERGIC AGONIST This invention was made at least in part with Government support under National Institutes of Health grant number DK 37116. The Government has certain rights in the invention.

This is a continuation-in-part of U.S. Ser. No. 07/499,610, filed Mar. 27, 1990, now U.S. Pat. No. 5,196,195 which has an inventor in common and the same assignee.

TECHNICAL FIELD

This invention is directed to a novel method of limiting biological nitric oxide formation.

BACKGROUND OF THE INVENTION

For several decades nitroglycerin has been administered to humans as a vasodilating agent in the treatment of cardiovascular disease. In about 1987, it was shown that nitroglycerin so administered is converted in the body to nitric oxide which is the pharmacologically active metabolite. Still more recently, nitric oxide has been shown to be formed in endothelial cells from arginine as a normal metabolite which is an important endothelium-derived relaxing factor (EDRF). It is now widely accepted that many naturally occurring substances which act as physiological vasodilators mediate all or part of their action by stimulating release of EDRF; these substances include acetylcholine, histamine, bradykinin, leukotrienes, ADP, ATF, substance P, serotonin, thrombin and others. EDRF is currently being intensively studied as participating in regulation of blood flow and vascular resistance. Incident to such study, a search has been carried out for compounds which inhibit nitric oxide production in the body. One compound discovered for use to obtain this effect is the arginine antagonist $N^G$-methyl-L-arginine (Sakuma, I., et al, Proc. Natl. Acad. Sci. USA 85, 8664–8667 (1988)). Administration of $N^G$-methyl-L-arginine to guinea pigs and rabbits has been shown to increase blood pressure (Aisaka, K., et al, Biochemical and Biophysic Research Communications, Vol. 160, No. 2, pp. 881–886, 4/28/89; Rees, D. D., et al, Proc. Natl. Acad. Sci. USA, Vol. 86, pp. 3375–3378, 5/89). Recently, it has been discovered that arginine antagonists inhibit systemic hypotension (Kilbourn, R. G. et al. U.S. Pat. No. 5,028,627) and that very effective arginine antagonists are physiologically active $N^G$-amino-L-arginine (Griffith, O. W. U.S. Pat. No. 5,059,712) and physiologically active $N^G$-(hydrazinoiminomethyl)lysine (Griffith, O. W., U.S. Pat. No. 5,132,453). It has also been discovered that the duration of the nitric oxide-mediated hypotensive response to acetylcholine is prolonged in animals infused with L-arginine (Aiaska, K., et al, Biochem. Biophys. Res. Commun. 163, 710–717, 1989).

In addition to vascular endothelium, macrophages have also been shown to produce nitric oxide in the body which is a component of their cell killing and/or cytostatic function (Iyengar, R., et al, Proc. Natl. Acad. Sci, USA, Vol. 84, pp. 6369–6373, 9/87). It has also been shown that addition of arginase to macrophage cell culture medium prevents the activated macrophage cytoxic effector mechanism (Hibbs, J. B., et al, The Journal of Immunology, Vol. 138, No. 2, 550–565, 1/87).

It is thought that in sepsis or cytokine-induced shock, induced production of nitric oxide plays an important role in the observed life-threatening hypotension and is a basis for the clinically observed insensitivity to pressor agents such as $\alpha_1$ adrenergic agonists used in the treatment of said hypotension. Very recently it has been discovered that administration of nitric oxide synthesis inhibitors in combination with $\alpha_1$ adrenergic agonists in the treatment of said hypotension, potentiates the action of the $\alpha_1$ adrenergic agonists by restoring vascular sensitivity to effects of said agonists. (Gross, S. S., et al, U.S. Pat. No. 5,216,025).

SUMMARY OF THE INVENTION

It has now been discovered that reducing plasma levels of endogenous arginine limits nitric oxide production in a subject in need of such limiting and that parenteral administration of an arginine depleting agent in an amount reducing the plasma arginine level effects this. The method herein is generally directed to limiting nitric oxide production in a subject in need of such limiting (whether or not said nitric oxide production has been pathologically stimulated) if said reduction provides a positive result and comprises effecting reduction of plasma level of endogenous arginine. An embodiment of this method comprises parenterally administering an amount of an arginine depleting agent to effect reduction of plasma level of endogenous arginine to a nitric oxide production limiting level.

In an important application of the method herein, the nitric oxide production limited is that by endothelial cells and/or vascular smooth muscle cells and the amount of arginine depleting is such as to cause an increase in diastolic blood pressure when diastolic blood pressure is low due to nitric oxide production.

In another important application of the method herein, a subject is treated for systemic hypotension caused by bacterial endotoxin-induced and/or cytokine-induced production of nitric oxide and the method herein comprises parenterally administering to said subject a pressor agent such as one or more $\alpha_1$ adrenergic agonists and an amount of arginine depleting agent to effect reduction of plasma level of endogenous arginine to a nitric oxide production limiting level sufficient to restore vascular contractile sensitivity to effects of $\alpha_1$ adrenergic agonists.

Preferably, the arginine depleting agent is arginase, and it is administered intravenously.

In one embodiment herein the arginine depleting agent is administered in a nitric oxide production reducing amount in conjunction with administration of an arginine antagonist in order to reduce the amount of arginine antagonist that would otherwise be administered to inhibit nitric oxide production. In this embodiment the amount of said antagonist administered is 10 to 80% less than a nitric oxide production inhibiting amount of said antagonist in the absence of arginase.

In still another embodiment, the arginine depleting agent is attached to polyethylene glycol or an insoluble support for parenteral administration or is contained in an extracorporeal reactor which is attached to the treated subject's blood supply.

The term "subject" is used herein to mean any mammal, including humans, where nitric oxide formation from arginine occurs.

The methods herein contemplate prophylactic as well as curative use.

DETAILED DESCRIPTION

Figure 1:
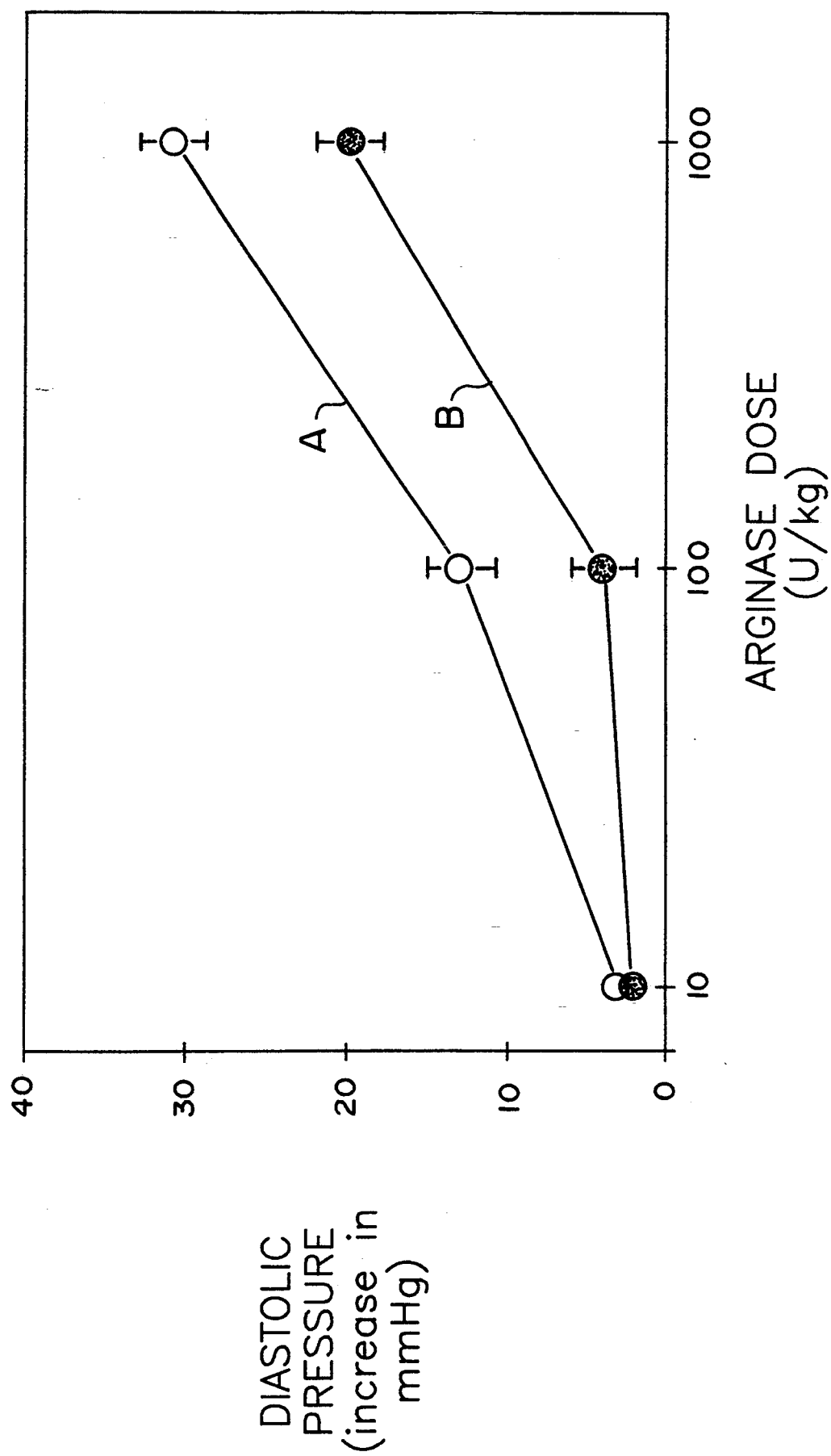
FIG. 1 depicts graphs of Diastolic Pressure as Arginase Dose which are results of Example I.

The methods herein control endogenous arginine levels to limit nitric oxide production in a subject in need of such limiting. This includes controlling endogenous arginine levels to maintain or obtain nitric oxide production at a level below pathological. In respect to controlling blood pressure, this includes controlling nitric oxide production to a level below that at which pathological decreases in blood pressure occur whether or not nitric oxide production is responsible for said pathological decreases (i.e., the invention includes lowering nitric oxide production to accommodate for blood pressure decrease which is caused by an agent other than nitric oxide). In respect to potentiating the action of $\alpha_1$ adrenergic agents in the treatment of bacterial endotoxin-induced or cytokine-induced hypotension, the invention includes lowering nitric oxide production to restore vascular contractile sensitivity.

As previously indicated, the administration route in the instant invention is parenteral. Parenteral administration includes, for example, intramuscular, intravenous, intraperitoneal, and subcutaneous and possibly rectal routes of administration. Preferably, the route of administration is intravenous, for example, at a concentration ranging from 10 to 10000 U/ml in saline or other non-toxic diluent, either as a bolus injection (one administration over 5 seconds or less) or as a continuous infusion. Alternatively, a response can be obtained by administering arginase attached to polyethylene glycol as either a bolus or continuous infusion or by circulating a portion of the subject's blood flow through an arginase-containing extracorporeal reactor.

The arginine depleting agent is any agent which when administered in a non-toxic amount so changes the character of plasma arginine that it does not function as a substrate for nitric oxide formation. Suitable arginine depleting agents include enzymes, for example, arginase, arginine decarboxylase, arginine decarboxylating oxygenase, and arginine deiminase. Arginase is the preferred arginine depleting agent herein. As is well known, it catalyzes the hydrolysis of L-arginine to L-ornithine and urea. Arginase is a commercially available enzyme that is normally present inside cells but not present in significant amounts in the plasma. Arginine decarboxylase and arginine decarboxylating oxygenase catalyze the decarboxylation of arginine. Arginine deiminase converts arginine to citrulline and ammonia.

We turn now to the subjects to be treated by the methods herein.

One group of subjects comprises those with pathologically low blood pressure.

One class within this group are those with idiopathic hypotension.

Another class within this group are those with drug-induced hypotension. In this case co-administration of arginine depleting agent with said drug pursuant to the method herein allows use of drugs that otherwise have unacceptable side effects.

Still another class within this group are those suffering from certain forms of shock (including toxic shock syndrome).

Another group of subjects comprises those with immune disorders in which down regulation of nitric oxide formation is advantageous, e.g., in inflammation or auto-immune disorders or in therapeutic immunosuppression for transplant purposes.

Turning now to dosage, such depends on the effect desired and the responsiveness of the individual subject. For example, for raising blood pressure, a blood pressure effective raising amount is administered. For use concurrently with $\alpha_1$ adrenergic agonist, a nitric oxide production limiting amount sufficient to restore vascular contractile sensitivity to the effect of the agonist, is administered. For disorders requiring immunosuppression, an immunosuppressive effective amount is administered. Generally, dosages of arginine depleting agent range from 10 to 5000 U/kg for a bolus intravenous injection and from 10 to 1000 U/kg/min for continuous infusion intravenous administration. A unit (U) is defined as the amount of arginine depleting agent necessary to covert 1 micromole of arginine to products per minute at physiological pH at 37° C.

We turn now to the method herein where arginine depleting agent administration is used in conjunction with administration of an arginine antagonist. It has been found herein that the arginine depleting agent potentiates the effect of the arginine antagonist such that the arginine antagonist is administered in an amount 10–80%, preferably 10–30%, less than a nitric oxide production inhibiting amount of said antagonist in the absence of arginine. For this purpose, the arginine depleting agent preferably is arginase administered intravenously in an amount ranging from 10 to 1000 U/kg/min. The arginine antagonist is preferably selected from the group consisting of L-$N^G$-aminoarginine, L-$N^G$-methylarginine and L-$N^G$-nitroarginine and $N^6$-(hydrazinoiminomethyl)lysine. A dosage of 0.1 to 10 mg/kg/minute of L-$N^G$-methylarginine administered intravenously in a bolus injection in conjunction with continuous intravenous infusion of 30 U/kg/minute of arginase has been found effective in raising diastolic blood pressure. The arginine antagonist can also be administered by continuous infusion. Arginase reacts very slowly or not at all with said antagonists so it has no practical effect on negating their functionality.

We turn now to the embodiments where arginase is used in conjunction with a carrier or is administered in an extracorporeal reactor to obtain longer duration of action and avoidance of antigenicity.

In one embodiment where the arginine depleting agent has a longer duration of action and results in a diminished antigenic response by the treated subject, methoxypolyethylene glycol (PEG) is attached to the said agent. The said agent is preferably arginase and the PEG is preferably of 5000 Daltons. Arginase and PEG are covalently coupled using 2,4,6-tricloro-s-triazine as described by K. V. Savoca et al. (Biochem. Biophys. Acta 578, 47–53 (1979)); PEG is attached to 50 to 60% of the free amino groups of arginase. Arginase modified in the manner described has a circulating half-life at least 10-fold greater than that of native unmodified arginase when injected intravenously in mice. Sera from mice administered native arginase contains anti-arginase antibodies whereas sera from mice administered PEG-modified arginase does not contain antibodies to either arginase or PEG-modified arginase.

In another embodiment where the arginine depleting agent has a longer duration or action and results in a diminished antigenic response by the treated subject, the said agent is attached to an extracorporeal reactor and the subject's blood is passed through said reactor. The said arginine depleting agent is preferably arginase and the said reactor can be a packed bed of Dacron fibers to which arginase is attached using gammaaminopropyltriethoxysilane and glutaraldehyde (general method of R. Y. C. Ko., et al, J. Biomed. Res 10 249–258 (1976)) or said reactor may be an insoluble carrier matrix of reconstituted bovine collagen containing arginase (general method of L. S. Olanof, et al, J. Biomed. Res. 8, 125–136 (1977)) or said reactor may be a conventional hollow fiber hemodialyzer to which arginase is attached covalently (general method of J. A. Jackson, et al, J. Pharmacol. Expt. Ther. 209, 271–274 (1979)). In each case the subject's blood is passed through the extracorporeal reactor by means of conventional arteriovenous cannulation wherein blood is removed from the subject through an arterial cannula, passed through the extracorporeal reactor, and then returned to the subject through a venous cannula. Use of an arginine depleting agent in an extracorporeal reactor is preferably employed in normotensive shock-prone subjects in which the necessary cannulation and perfusion apparatus can be placed in service before the subject is overtly hypotensive.

We turn now to the application where a subject is treated for systemic hypotension caused by bacterial endotoxin-induced and/or cytokine-induced production of nitric oxide where pressor agent such as, $\alpha_1$ adrenergic agonist is administered in conjunction with the arginine depleting agent. Arginine depleting agents and suitable dosages thereof are discussed above. The $\alpha_1$ adrenergic agonists include the known pressor agents including phenylephrine, epinephrine, norepinephrine, dopamine, metariminol, methoxamine, ephedrine and mephentermine. Another pressor agent is angiotensin. The pressor agents are utilized in an amount sufficient to cause increase in diastolic blood pressure in conjunction with the restored vascular contractile sensitivity.

The invention is illustrated in the following examples:

EXAMPLE I

A male Hartley guinea pig weighing about 300 grams is anesthetized with sodium pentobarbital (50 mg/kg i.p.) and a tracheal canula is inserted. The left carotid artery is cannulated and connected to a physiological pressure transducer. Blood pressure tracings are displayed on a physiograph. Diastolic blood pressure is monitored and an intravenous administration by bolus injection (0.2 ml) of 10 U/kg arginase, 100 U/kg arginase, 1000 U/kg arginase (in saline) is given and also these same injections are administered to a guinea pig given L-arginine (30 mg/kg in 0.2 ml saline) and continuously infused with 10 mg/kg/minute of L-arginine in saline (concentration of 120 mg/ml). The results (mean values±standard error) from studies with 4 guinea pigs are depicted in FIG. 1 where line A (open circles) depicts transient results where only bolus injections of arginase were used and line B (closed circles) depicts transient results where bolus injections of arginase were given together with L-arginine. Line A shows that the blood pressure of the guinea pig increases transiently when either 100 U/kg or 1000 U/kg arginase is given as a bolus injection. Line B shows the effect is reduced when L-arginine is given along with the arginase. FIG. 1 (line A) establishes that nitric oxide is continuously formed in a normal guinea pig and is transiently reduced on bolus intravenous administration of 100 U/kg or 1000 U/kg of arginase whereby arginine is removed from the plasma by conversion to ornithine and urea by the arginase. FIG. 1 (line B) suggests that the increase in blood pressure is due to removal of plasma arginine since, if arginine is simultaneously replaced, the increase in blood pressure is less.

While Example I is reproducible, the blood pressure increase in Example I is observed only transiently and therefore may not be due to the arginase but rather to an impurity in the arginase which provides a transient pressor effect. This conclusion is based on the results of Example IV which indicates no or little effect of arginase administration at a longer time after administration when arginase should still be present because of its half life.

EXAMPLE II

Acetylcholine is known to stimulate arginine-dependent nitric oxide formation and thereby cause a fall in blood pressure. Administration of acetylcholine to guinea pigs thus provides a model for the pathological overproduction of nitric oxide and resultant hypotension characteristic of septic shock and some other forms of shock. It has been shown in studies wherein excess arginine was administered that increased L-arginine availability extends the duration of acetylcholine-induced hypotension (Aisaka, K., et al Biochem. Biophys, Res. Commun. 163, 710–717 1989)). The studies below show that diminished L-arginine availability decreases the extent or duration of acetylcholine-induced hypotension.

Figure 2:
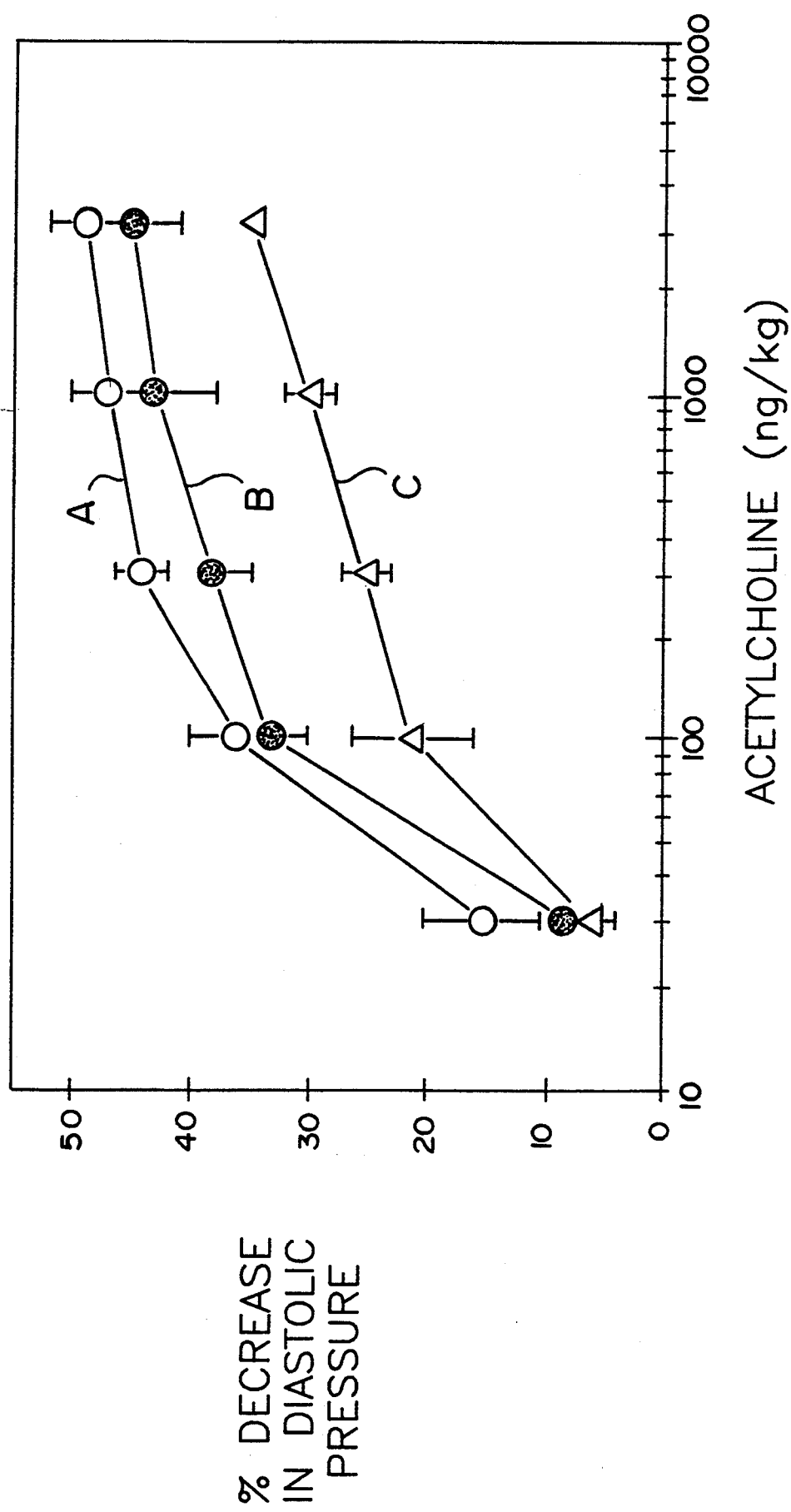
FIG. 2 depicts graphs of % Decrease in Diastolic Pressure vs. Acetylcholine which are results of Example II.

The effect of arginase on the acetylcholine-mediated hypotension in guinea pigs was determined using the general method described in Aisaka, K., et al, Biochem, Biophys, Res. Commun. 163, 710–717 (1989). The dose of acetylcholine ranged from 30 ng/kg to 3000 ng/kg. The results are shown in FIG. 2. Results with infusion with saline (0.25 ml/min) are depicted in line A (open circles). Results with infusion with 100 U/kg/min arginase in saline (concentration of 4000 U/ml) are depicted in line B (closed circles). Results with infusion with 300 U/kg/min arginase in saline (concentration of 12000 U/ml) are depicted in line C (open triangles). The results show that the extent of nitric oxide formation is dependent on the level of circulating L-arginine. When nitric oxide production was stimulated to levels simulating those seen in mild pathological shock conditions (mimicked here by acetylcholine administration), administering arginase depleted circulating arginine and limited the fall in blood pressure.

Constant rate infusion of arginase (100 or 300 U/kg/min, i.v.) without pathological stimulation did not change arterial pressure significantly.

EXAMPLE III

An experiment was carried out to determine the effect of intravenous arginase administration as follows: Guinea pigs (male Hartley guinea pigs, 250–300 gm) were determined to have an initial plasma arginine level of 45 $\mu$M. After giving arginase (300 units/kg per min for 20 min), plasma arginine levels were 27 $\mu$M, 6 $\mu$M, <1 $\mu$M, <2 $\mu$M and <2 $\mu$M at 5, 10, 15, 20 and 25 min. after beginning arginase infusion, respectively. Arginase was administered intravenously through a canula placed in the right jugular vein. Blood (400 $\mu$l) was drawn at the times indicated through a canula placed in the left carotid artery and was immediately centrifuged for 1 min. to obtain plasma. The plasma was rapidly mixed with an equal volume of 0.1M HCl containing 0.25 mM canavanine (internal standard). A protein-free ultrafiltrate was obtained by centrifugation through a 10,000 Mr cut-off membrane (Millipore Ultrafree-MC). Amino acids were determined in the ultrafiltrate (100 µl) after reaction with 40 µl of a cocktail containing methanol:phenylisothiocyanate:water:triethylamine (7:1:1:1; PicoTag reagent) and fractionation by reverse-phase HPLC as described by Davey, J. F. and Ersser, R. S., J. Chromatog. 528, 9-23 (1990).

In similar studies to that described above, but with pithed rats, initial arginine levels were 111 to 132 µM and levels following arginase administration were 4 to 32 µM.

EXAMPLE IV

This example is provided to demonstrate the correlation between plasma arginine levels and blood pressure. More specifically, the present example demonstrates a correlation between low plasma arginine levels and increased blood pressure in endotoxin-treated animals.

The enzyme arginase was used to reduce plasma arginine levels in Spraque-Dawley rats (Weight per rat=250-300 gm). Arginase is an enzyme that irreversibly converts L-arginine to L-ornithine+urea. The rats were anesthetized with ethyl ether and then pithed as described by Gillespie, J. S., et al, Br. J. Pharmacol. 30, 78-87 (1967). The animals were pithed prior to use in the present study so as to eliminate any reflex control of blood pressure by the central nervous system.

Arginase was dissolved in sterile saline (1000 I.U./ml) and was administered by intravenous infusion at a rate of 300 I.U./min. for 20 min. One I.U. is the amount of arginase that converts 1 µmol of arginine to products per minute. The administration of arginase to pithed rats with or without exposure to endotoxin (15 mg/kg dose, ip), according to the dose outlined above, resulted in a decrease in plasma arginine levels of from about 150 µM to $\leq 4$ µM within a few minutes. Plasma arginine remained at levels $\leq 4$ µM for at least 1 hour after the arginase infusion was stopped.

To record blood pressure, a tracheotomy was first performed on each rat, after which the rats were artificially respired with room air. The left common carotid artery was then cannulated in each rat for blood pressure measurement via a Statham pressure transducer (Hato Rey, Puerto Rico) and displayed on a physiogram (Grass Instruments, Qunicy Mass.). Heart rate was measured from the lead III electrocardiogram.

Two separate groups of animals were examined. The first group of animals, designated the "control" group, received no endotoxin. The blood pressure of the "control" group animals was measured at two different times, once before the administration of arginase and once after the administration of arginase.

The second group of animals, designated the endotoxin group, received a single dose of endotoxin of 15 mg/kg body weight, which was administered at least 6 hours prior to any subsequent arginase treatment. The blood pressure of all animals in both treatment groups was then measured at two different times, again once before arginase treatment and once after arginase treatment.

The results from this example are presented in Table 1.

TABLE 1

EFFECT OF REDUCED PLASMA ARGININE ON BLOOD PRESSURE

| | No Arginase | | Arginase |
|---|---|---|---|
| | B.P. (mm Hg) | Average B.P. | B.P. (mm Hg) |
| Control Rats | | | |
| 1 | 61 | 59.8 ± 1.3 | 61 |
| 2 | 60 | | 60 |
| 3 | 60 | | 64 |
| 4 | 58 | | 68 |
| Endotoxin Rats (1.5 mg/Kg) | | | |
| 1 | 36 | 33.2 ± 3.3 | 44 |
| 2 | 34 | | 40 |
| 3 | 28 | | 28 |
| 4 | 32 | | 36 |
| 5 | 36 | | 44 |

Blood pressure readings for 4 control pithed rats were 61, 60, 60, and 58 mm Hg (average 59.8±1.3 mm Hg) (See Table 1). Following administration of arginase, blood pressure was unchanged in two rats and increased by 4 and 10 mm Hg in 2 other rats (average increase 3.5±4.7 mm Hg, not statistically significant).

Blood pressure readings for 5 rats at 6 hours after giving 15 mg/kg lipopolysaccharide (endotoxin) by intravenous injection was 36, 34, 28, 32, and 36 mm Hg (average 33.2±3.3 mm Hg, See Table 1). Note that the endotoxin-treated rats were clearly hypotensive relative to the controls.

Following administration of arginase, blood pressure in the endotoxin-treated rats increased by 8, 6, 0, 4, and 8 mm Hg (average increase 5.2±3.3 mm Hg). The average blood pressure increase following arginase treatment of the endotoxic, pithed rats was 15.7% (statistically significant, $p<0.05$).

In a second study carried out using the same protocol, it was found that 5 control rats had basal mean arterial pressure of 55.9±1.6 mm Hg and that this changed insignificantly following administration of arginase (change=−0.54±1.8 mm Hg). Five rats given endotoxin had a basal mean arterial pressure of 34.3±3.8 mm Hg and this increased by 7.0±1.5 mm Hg following administration of arginase. This increase of 20.4% was statistically significant ($p<0.05$).

Overall, this study shows that reducing plasma arginine levels has no significant continuing effect on blood pressure in control animals, but did have a significant effect on blood pressure readings in endotoxic animals. The lack of a demonstrated continuing effect in control animals may be due to the slow rate of nitric oxide formation in control animals, so as to negate any requirement for exogenous (i.e. plasma) arginine. Thus, a reduction in plasma arginine levels in such animals would not be a limiting factor for generating nitric oxide.

In contrast, the rate of nitric oxide formation in endotoxic animals is much faster than in control (non-endotoxic) animals, and results in the development of hypotension. In these endotoxic animals, the cells making nitric oxide must obtain extra arginine from the plasma. When plasma arginine is very low in endotoxic animals (i.e. after arginase administration), there is not enough arginine available to sustain a pathologically high rate of nitric oxide synthesis by cells associated with blood vessel walls (i.e., endothelial cells and/or vascular smooth muscle cells). Thus, the rate of nitric oxide formation is reduced, resulting in a concomitant reduction in the extent of blood pressure reduction in the vasculature of the animal. Thus, depletion of serum arginine levels could be used to effect an increase in blood pressure in hypotensive animals.

EXAMPLE V

The present example is provided to demonstrate the correlation between low plasma arginine levels and increased response to pressor agents in vivo in endotoxin-treated animals. The particular pressor agent employed in this example is phenylephrine. However, virtually any pressor agent could be employed with equal utility to demonstrate the physiological effects disclosed by the present inventors. It has previously been observed that in septic shock, patients are hypotensive and no longer respond well to the usual pressor drugs such as phenylephrine. To determine if lowering plasma arginine would improve responsiveness, a study was carried out in pithed rats.

Animals were pithed as described in Example IV. Blood pressure measurements were obtained also as described in Example IV. Arginase was also prepared according to the method described in Example IV.

Both left and right jugular veins were cannulated for drug administration; and left jugular was used for bolus administration of phenylephrine and the right jugular vein was used for continuous infusion of arginase. All animals from both groups (Control and Endotoxin) received phenylephrine in sequential doses of 0.3, 1.0, 2.0, and 6.0 µg/kg. Each group had 5 rats. Basal blood pressure valves are given in the second study of Example IV.

The results from this example are presented in Table 2.

TABLE 2

EFFECT OF ARGINASE AND ENDOTOXIN ON THE PRESSOR EFFECT OF PHENYLEPHRIN

| Phenylephrine dose | BLOOD PRESSURE INCREASE (mm Hg) | |
|---|---|---|
| | Without Arginase Ave. ± S.D. | With Arginase Ave. ± S.D. |
| Study #1: Control Animals | | |
| 0.3 µg/Kg | 18.2 ± 3.9 | 16.9 ± 2.0 |
| 1.0 µg/Kg | 32.4 ± 3.2 | 32.2 ± 4.5 |
| 2.0 µg/Kg | 50.7 ± 3.8 | 49.1 ± 5.4 |
| 6.0 µg/Kg | 83.4 ± 10.1 | 84.0 ± 9.7 |
| Study #2: Endotoxic Animals | | |
| 0.3 µg/Kg | 4.9 ± 1.6 | 9.6 ± 2.1 |
| 1.0 µg/Kg | 11.6 ± 3.3 | 19.7 ± 4.0 |
| 2.0 µg/Kg | 22.1 ± 6.3 | 34.3 ± 8.3 |
| 6.0 µg/Kg | 54.3 ± 12.0 | 64.7 ± 12.2 |

This example shows the effects of endotoxin and of arginase on mean systolic blood pressure response to phenylephrine in pithed rats. Endotoxin (15 mg/kg body weight) was given by intravenous injection 6 hrs before the experiment began; arginase (300 I.U./Min. for 20 min.) was given intravenously to each rat after the "Without Arginase" measurements were made.

Table 2 shows the mean maximum increase in blood pressure following the phenylephrine doses indicated for each group. Each rat in the group was tested first without arginase (at 0.3, 1.0, 2.0 and 6.0 µg/kg phenylephrine, in sequence) and was then retested with phenylephrine in the same dose and sequence after arginase treatment.

This data demonstrates that reducing plasma arginine levels through arginase treatment, enhances the pressor agent (such as phenylephrine) response in endotoxic animals, reducing the difference observed between endotoxic and control animal blood pressure increases at the same pressor agent dose. Moreover, endotoxic animals pretreated with arginase demonstrated pressor response comparable on a percent increase basis to the pressor response observed in endotoxic animals receiving no arginase (See Table 2 and the second study of Example IV).

Endotoxin decreases an animals ability to present the normal hypertensive response (i.e., increase in blood pressure) to phenylephrine. Thus, compare the "Without Arginase" data of control and endotoxic rats at each dose of phenylephrine (Table 2). This effect occurs because the endotoxic animals are making large amounts of nitric oxide from arginine, and that causes hypotension and blunting of the response to phenylephrine.

Arginase administration improves the hypertensive response to a pressor agent, such as phenylephrine. Smaller differences were observed between control and endotoxic animals given arginase (indicating only a small loss of responsiveness) relative to the larger differences between control and endotoxic animals not given arginase (indicating a large loss in responsiveness).

For example, at a phenylephrine dose of 6 µg/Kg, in animals not given arginase (i.e., having a higher serum arginine concentration), the pressor response to phenylephrine drops from 83.4±10.1 mm Hg (a pharmacologically useful pressor agent response) in control animals to 54.3±12.0 mm Hg (a poor pressor agent response) in endotoxic animals, a difference in pressor response of 29.1 mm Hg. In contrast, at the same phenylephrine dose in animals given arginase (i.e., decreased serum arginine levels), the pressor response in control and endotoxic animals was 84.0±9.7 and 64.7±12.2, respectively, a difference of only 19.3 mm Hg. Thus, depletion of plasma arginine with arginase significantly restores the "normal" (hypertensive) response to pressor drugs, such as phenylephrine.

The term "arginine depleting agent" is used herein to mean enzyme, e.g., arginase, used in unmodified state as well as the enzyme modified to obtain longer duration of action, for example, by attachment by covalent coupling to methoxypolylene glycol for administration or the enzyme modified for use in an extracorporeal reactor by attachment to Dacron fibers or by covalent bonding to a hollow fiber hemodialyzer or in a collagen matrix.

Many variations of inventive embodiment will be obvious to those skilled in the art. Thus, the inventive embodiments are defined by the claims.

What is claimed is:

1. A method for treating a subject for systemic hypotension caused by sepsis or cytokine induced production of nitric oxide, said method comprising administering to a subject in need of said treatment at least one $\alpha_1$ adrenergic agonist in a therapeutically effective amount and administering to said subject an amount of a plasma arginine depleting enzyme to reduce the plasma level of arginine to a nitric oxide production limiting level to restore vascular contractile sensitivity to the effects of said $\alpha_1$ adrenergic agonist, said enzyme being administered parenterally or by using an extracorporeal reactor which contains the enzyme and through which the subject's blood is passed.

2. The method of claim 1 wherein the arginine depleting enzyme is arginase.

3. The method of claim 2 wherein the arginase is administered intravenously.

4. The method of claim 1 wherein the $\alpha_1$ adrenergic agonist is selected from the group consisting of phenylephrine, epinephrine, norepinephrine, dopamine, metaraminol, methoxamine, ephedrine and, mephentermine.

5. The method of claim 1 wherein the $\alpha_1$ adrenergic agonist is selected from the group consisting of phenylephrine, norepinephrine and dopamine and is administered intravenously and the arginine depleting enzyme is administered in a plasma arginine level depleting amount ranging from 10 to 5000 U/kg.

* * * * *